United States Patent [19]

Tomoda

[11] Patent Number: 5,048,526
[45] Date of Patent: Sep. 17, 1991

[54] GAS JET SHOOTING DEVICE FOR USE WITH A NON-CONTACT TONOMETER

[75] Inventor: Hideo Tomoda, Tokyo, Japan

[73] Assignee: Kabushiki Kaisha Topcon, Japan

[21] Appl. No.: 234,043

[22] Filed: Aug. 19, 1988

[30] Foreign Application Priority Data

Aug. 20, 1987 [JP] Japan .................... 62-207054
Sep. 1, 1987 [JP] Japan .................... 62-216531

[51] Int. Cl.$^5$ .............................. A61B 3/16
[52] U.S. Cl. ............................ 128/648; 417/553
[58] Field of Search ............. 128/645, 648; 417/415, 417/443, 445, 446, 496, 553

[56] References Cited

U.S. PATENT DOCUMENTS

| | | | |
|---|---|---|---|
| 3,585,849 | 6/1971 | Grolman | 128/648 |
| 3,994,307 | 11/1976 | Loeffler | 417/415 |
| 4,770,181 | 10/1988 | Tomoda | 128/648 |
| 4,834,105 | 5/1989 | Matthews et al. | 128/648 |

Primary Examiner—William E. Kamm
Assistant Examiner—Kevin Pontius
Attorney, Agent, or Firm—Finnegan, Henderson, Farabow, Garrett and Dunner

[57] ABSTRACT

A gas jet shooting device for use with a non-contact tonometer, having a hollow head (19) with a nozzle (27) secured thereto, a cylinder (10) which communicates with the head, and a piston (11) reciprocatably mounted in the cylinder and defining a compression chamber (14) in the cylinder, and a linear d.c. motor (31) for driving the piston (11) for compressing the gas in the cylinder (10), the compressed gas being allowed to issue through the nozzle. The cylinder (10) is fed with the gas through a passage which opens into the chamber (14) and which does not include the nozzle. The gas may be air, and drawn into or pushed into the chamber through a filter (F). It may also be a gas other than air, harmless to the eye, supplied from a reservoir through a filter. Such arrangement ensures that air-born dust or tear drops scattered by the air jet will not be drawn into the chamber, and the device can therefore be maintained hygienic.

13 Claims, 6 Drawing Sheets

GAS JET SHOOTING DEVICE FOR USE WITH A NON-CONTACT TONOMETER

FIELD OF THE INVENTION

The present invention relates to a gas jet shooting device for use in a non-contact tonometer for shooting a jet, or puff, of gas toward the subject eye. The device is arranged to compress a gas for measurement in a cylinder, feed the thus compressed gas into a chamber defined in a head having a nozzle secured thereto, and allow the compressed gas to issue from the chamber through the nozzle forming the gas jet. The gas used for measurement is normally air, but other gases not harmful to the eye may also be used.

BACKGROUND OF THE INVENTION

Figure 7:
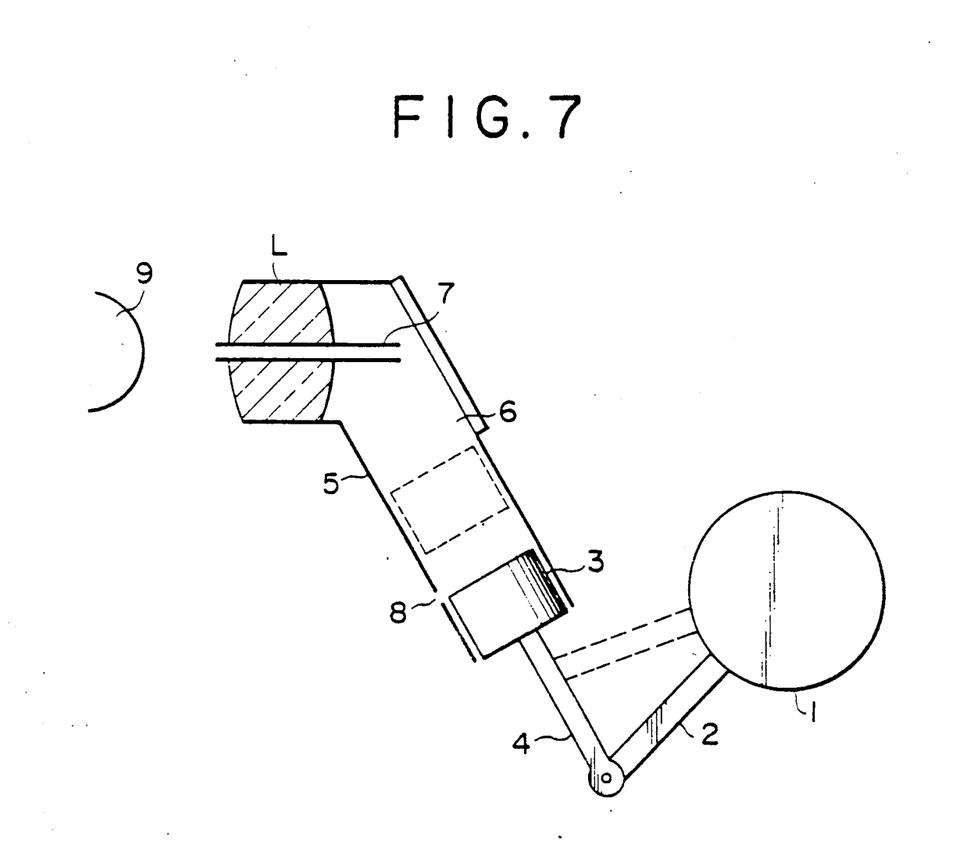
FIG. 7 is a schematic representation of a prior art gas jet shooting device for use with a non-contact tonometer.

FIG. 7 shows a prior art gas jet shooter of the above-defined type for use in a non-contact tonometer.

The gas jet shooter has a rotary solenoid 1 having an arm 2 connected to a piston rod 4 integral with a piston 3 which is mounted in a cylinder 5. A compression chamber 6 is defined within the cylinder 5, which is communicated with a nozzle 7 secured to a head L. The nozzle 7 is to be directed toward the subject eye. The rotary solenoid 1 will, when energized with an electric current, turn the arm 2 in the clockwise direction; the arm 2 will turn back to the original position under the elastic action of a spring (not shown) upon deenergization of the rotary solenoid. An exhaust port 8 is formed in the lower portion of the cylinder 5 for allowing the exhaust of air from the compression chamber 6 in the initial phase of the compressing process.

In operation, the piston 3 is driven upward with the piston rod 3 by energizing the rotary solenoid 1 to turn the arm 2 in the clockwise direction, whereby the pressure in the compression chamber 6 is made higher and the compressed high-pressure air from the compression chamber is shot against the subject eye 9 through the nozzle 7. The tonometer having the gas jet shooting device incorporated therein will make a measurement in a known manner while the air jet is thus shot against the subject eye.

Upon completion of the air jet shooting operation, the rotary solenoid 1 is deenergized to return back to the original position under the elastic action of the spring (not shown) and the piston 3 is moved downward accordingly. Thus, the pressure in the compression chamber will lower and air is drawn into the compression chamber 6 from around the subject eye 9 through the nozzle 7.

The air drawn into the compression chamber 6 after the air shooting operation may carry foreign particles such as dust born in air, or tear particles scattered into air by the air jet, which would be shot together with the air against the subject eye in the next air jet shooting operation. The prior art device is thus disadvantageous from the point of view of hygiene

SUMMARY OF THE INVENTION

An object of the present invention is therefore to provide a gas jet shooting device for use in a non-contact tonometer which is constructed such that air-born dust or fine tear drops scattered into air by the air jet shooting operation will not be drawn into the compression chamber through the nozzle when the piston is withdrawn to its starting position.

To achieve this object, the gas jet shooting device for use with a non-contact tonometer according to one aspect of the present invention, arranged to compress a gas for measurement in a cylinder, feed the thus compressed gas into a chamber defined in a head having a nozzle secured thereto, and allow the gas to issue from the chamber through the nozzle forming the gas jet, is provided with means for feeding said chamber with the gas for measurement through a passage which opens into said chamber and which does not include said nozzle.

To achieve the object, the gas jet shooting device for use with a non-contact tonometer, arranged to compress air in a cylinder thus to issue the compressed air through a nozzle toward the subject eye, is provided with means for allowing air to be drawn into the cylinder from a region remote from the nozzle when the pressure in said cylinder is a negative pressure.

BRIEF DESCRIPTION OF THE DRAWINGS

The present invention will now be described, by way of example, with reference to the accompanying drawings, in which.

DESCRIPTION OF THE PREFERRED EMBODIMENTS

FIRST EMBODIMENT

Figure 1:
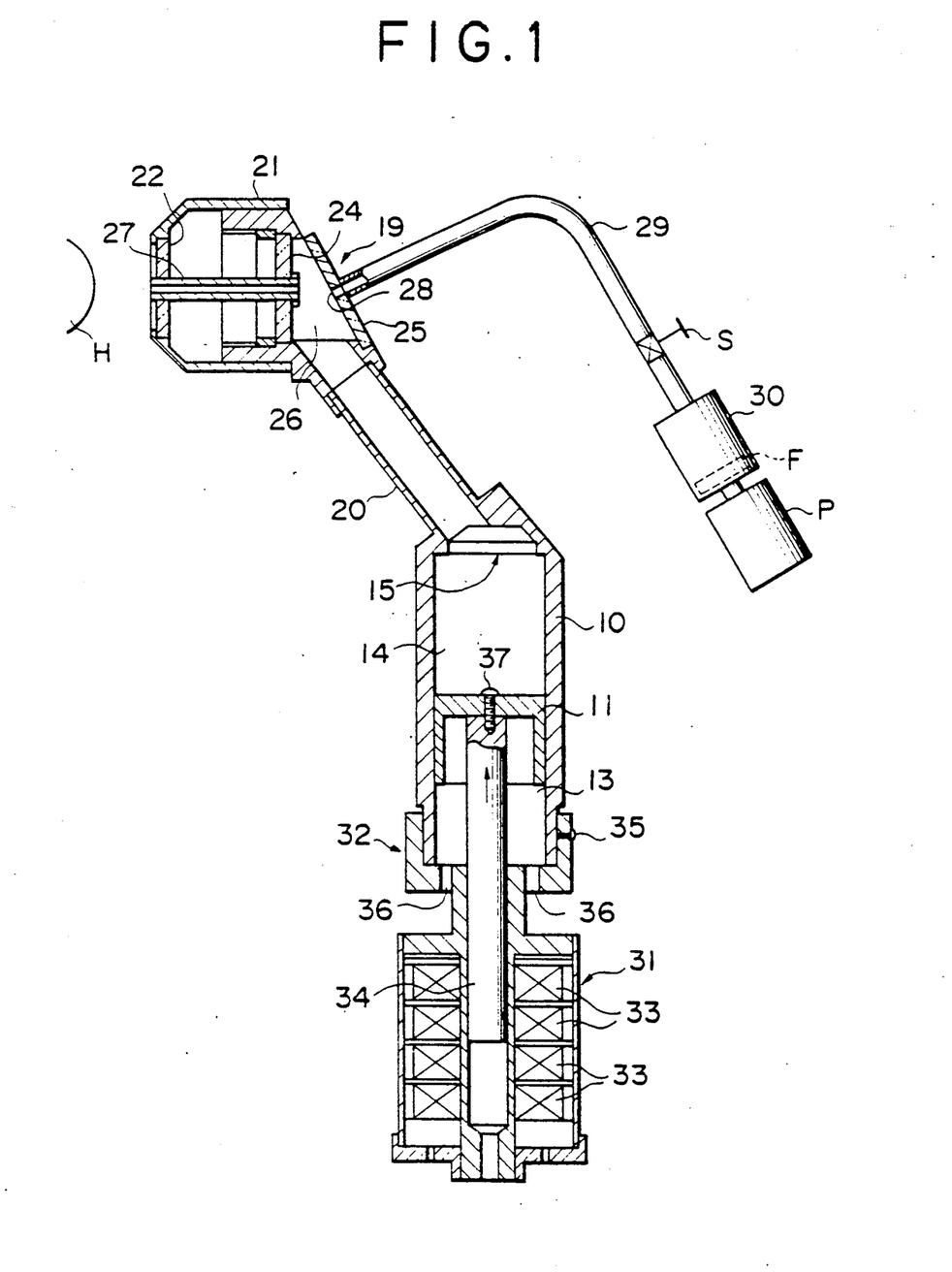
FIG. 1 is a cross sectional view of a first embodiment of the gas jet shooting device for use with a non-contact tonometer.

Referring first to FIG. 1, there is shown a first embodiment of the gas jet shooting device having a cylinder 10 in which a cylindrical piston 11 is reciprocatable. The piston 11 divides the space in the cylinder 10 into an upper compression chamber 14 and a lower chamber 13 opening into the atmosphere.

A stepped outlet port 15 is formed in the top wall of the cylinder 10, which connects the compression chamber 14 with the interior of a hollow head 19 through a flexible tube 20 made of e.g. rubber or synthetic resin.

The head 19 comprises a barrel 21, a front plate 22 secured thereto, a dividing plate 24 fitted within the barrel 21, and a rear plate 25 closing the barrel. The dividing plate 24 and the rear plate 25 in combination define a chamber 26 within the head 19. The gas used for measurement by the tonometer, air in this example, is compressed in the compression chamber 14 in the cylinder 10 and is supplied through the flexible tube 20 to the chamber 26 in the tonometer head 19. The compressed air is allowed to issue from the chamber 26 in the tonometer head 19 against the subject eye H through a nozzle 27, thus forming a jet or puff of air which will dent the cornea of the subject eye H. The nozzle is mounted in the head barrel 21 and extends through the front plate 22 and the dividing plate 24.

The head chamber 26 is also connected to an air reservoir 30 through a supply port 28 formed in the rear plate 25 and through a communicating tube 29 which has a restrictor S provided therein. The air reservoir 30 is fed with slightly compressed air from a compresser P via a filter F. The compressed air accumulated in the reservoir 30, cleared of impurities by means of the filter F, is supplied to the chamber 26 through the communicating tube 29, whereby a positive pressure is maintained in the chamber 26 at all times. The compresser P and associated elements including the supply port 28 constitute air supply means.

A linear d.c. motor 31, acting as a linear actuator for driving the piston 11, is coaxially secured to the end of the cylinder 10 in which the atmospheric chamber 13 is defined. The linear d.c. motor 31 comprises a bobbin 32 fitted at one end thereof on the cylinder 10, coils 33 wound on the bobbin 32, and a permanent magnet rod 34 axially movably inserted into the bobbin 32. The bobbin 32 is fixed at one end to the cylider 10 by means of a screw 35. Communicating holes 36 are formed in the end of the bobbin 32, which connect the chamber 13 to the atmosphere. The permanent magnet rod 34 is secured at one end to the piston 3 by means of a screw 37. The linear motor 31 is arranged such that the permanent magnet rod 34 is driven into or away from the compression chamber 14 by a magnetic field which is produced by passing a current through the coils 33 thus to polarize the bobbin 32 in the same direction as the polarization of the permanent magnet rod 34 or in the opposite direction, respectively.

The operation of the gas jet shooting device for use with the tonometer constructed as above will now be described.

First of all, the compressor P is actuated to feed the air reservoir 30 with compressed air through the filter F which removes impurities from the compressed air. The compressed and purified air accumulated in the air reservoir 30 is supplied to the head chamber 26 through the communicating tube 29 and through the supply port 28, whereby the chamber 26 is maintained at a positive pressure. That positive pressure is adjusted by means of the restrictor S to a pressure value which will not significantly affect the measurement to be taken.

Figure 2:
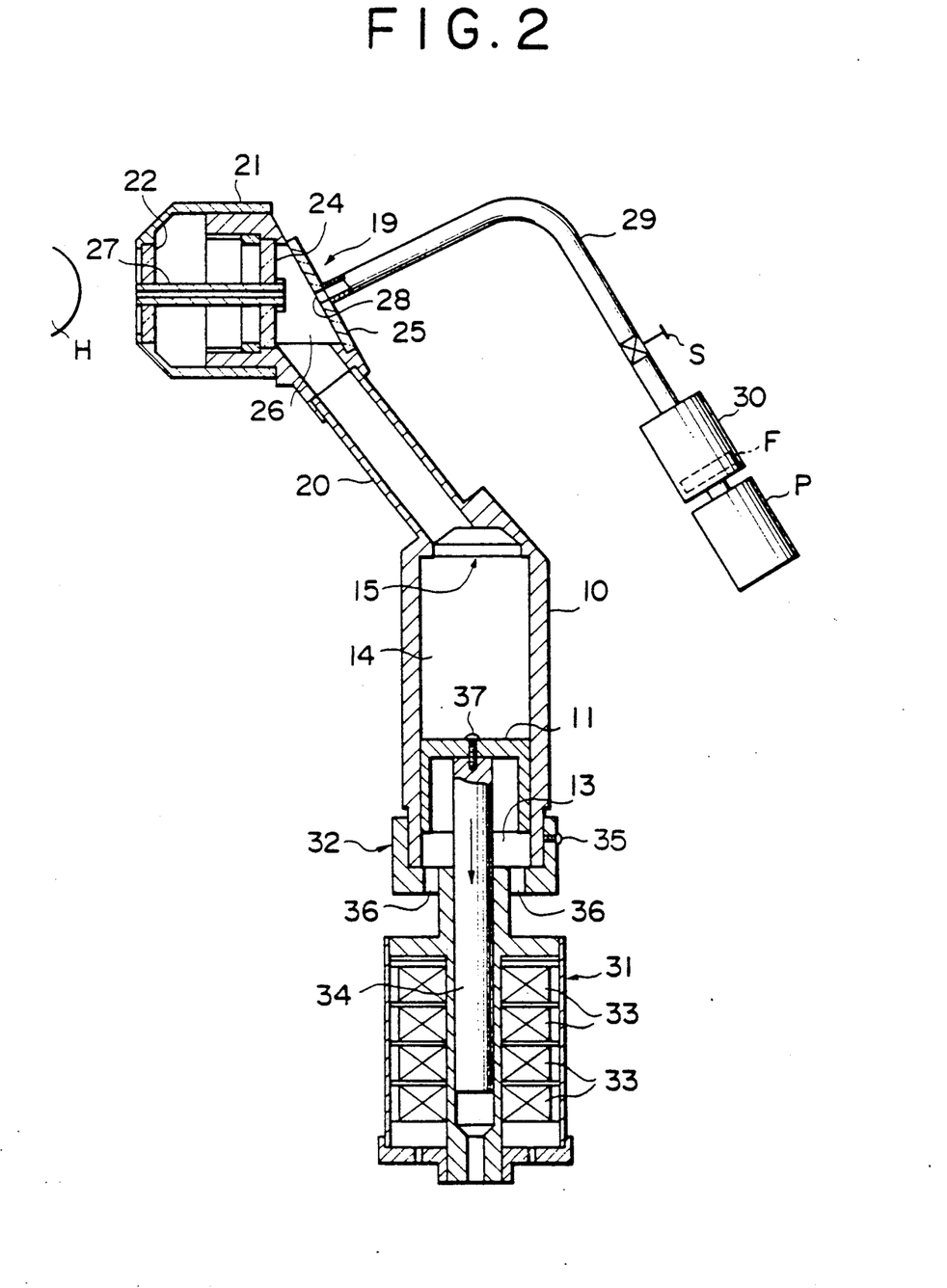
FIG. 2 is another cross sectional view of the device, showing the piston at its lowered position.

Then, a current is passed through the coils 33 of the linear d.c. motor 31 such as to polarize the bobbin 32 in the same direction as the permanent magnet rod 34. The rod 34 is driven into the compression chamber by the magnetic interaction between the permanent magnet rod itself and the magnetic field established by the current through the coils 33; the piston 11 is moved upward with the rod 34. The piston 11 will compress the air within the compression chamber 14 while moving upward, and the thus compressed air will flow into the chamber 26 in the tonometer head 19 and will issue from the tonometer head 19 through the nozzle 27, forming an air jet. The air jet is directed toward the subject eye H for the measurement of the intraocular pressure. Upon completion of the issuance of the air jet, the direction of the current through the coils 33 of the linear d.c. motor 32 is reversed to polarize the bobbin 31 in the opposite direction with respect to the permanent magnet rod 34. The rod 34 is then drawn downward by the magnetic force (see FIG. 2). The downward movement will reduce the pressure in the compression chamber 14 and accordingly the air is drawn from the head chamber 26 into the compression chamber 14. Since, at that time, slightly compressed purified air is supplied to the head chamber 26 from the air reservoir 30 through the communicating tube 29 and supply port 28, external air is not drawn through the nozzle 27 into the tonometer head and the associated cylinder 10. The purified air thus drawn into the cylinder is used for the next measurement.

The device therefore overcomes the problem associated with the previously mentioned prior art that airborn dust or fine tear drops scattered into air by the air jet shot against the subject eye during one measurement are drawn into the compression chamber upon completion of the one measurement and are subsequently shot against the next subject eye during the next measurement.

SECOND EMBODIMENT

Figure 3:
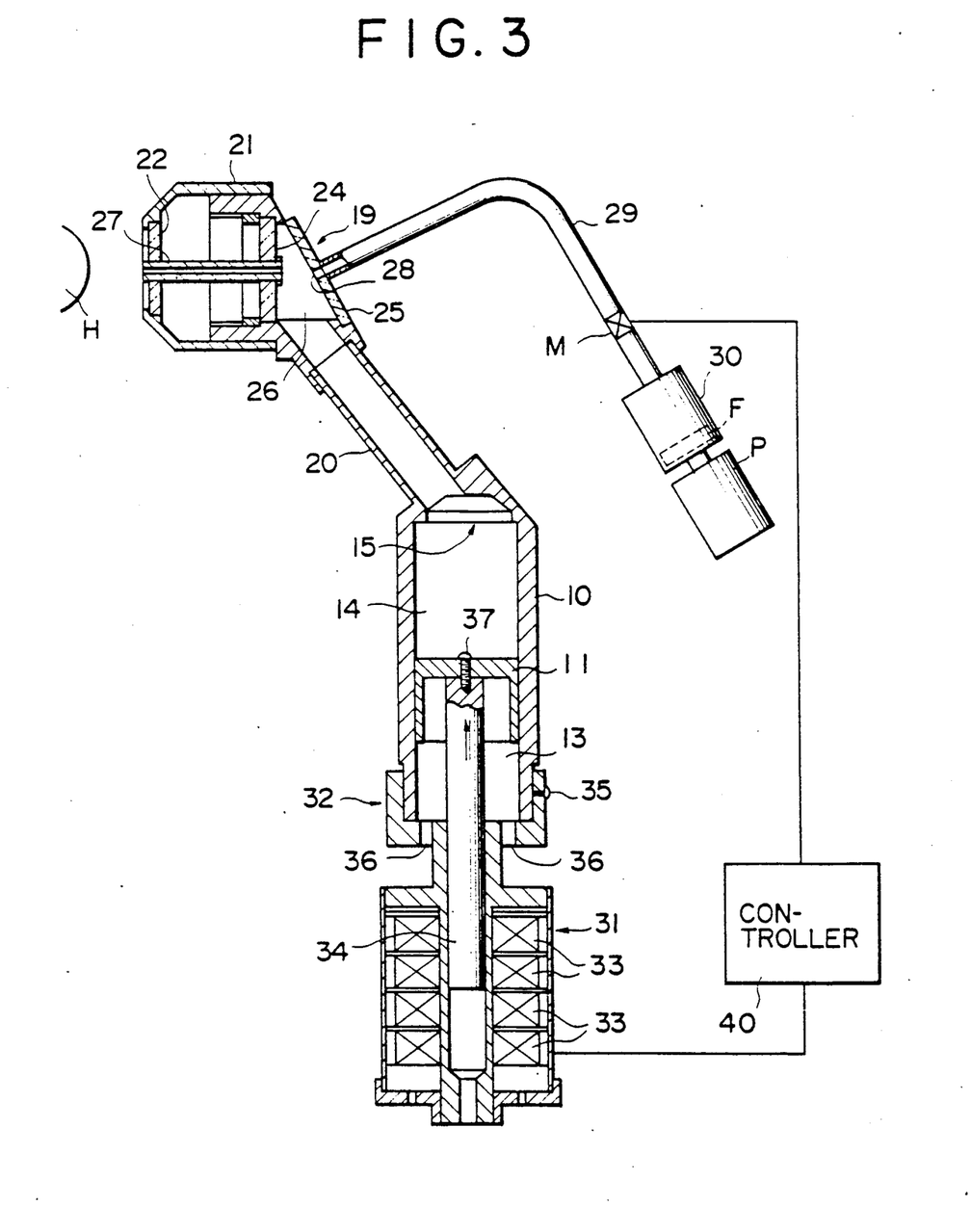
FIG. 3 is a cross sectional view of a second embodiment of the present invention.

FIG. 3 shows a second embodiment which differs from the embodiment of FIG. 1 only in that a normally closed electromagnetic valve M is provided in the communicating tube 29 in place of the restrictor S, and that a controller 40, which comprises e.g. a microcomputer, is provided to control the electromagnetic valve M and the linear motor 31.

The operation of the second embodiment is as follows:

Firstly, the air reservoir 30 is fed with air which has been compressed by the compressor P and purified by the filter F. The valve M is normally closed and thus the compressed air held in the air reservoir 30 will not flow into the head chamber 26.

Then, the controller 40 causes a current to pass through the coils 33 of the linear d.c. motor 31 so as to polarize the bobbin 32 in the same direction as the permanent magnet rod 34 thus to drive the piston 11 upward. The piston 11 will compress the air in the cylinder 10 while moving upward, and the thus compressed air is shot agaist the subject eye H through the nozzle 27. Upon completion of the air jet shooting operation, the controller 40 will reverse the direction of the current through the bobbin 32 of the linear d.c. motor 31 so as to reverse the direction of polarization of the bobbin 32 with respect to the permanent magnet rod 3, and at the same time it will cause the electromagnetic valve M to open. The compressed air in the reservoir 30 is thus allowed to flow into the head chamber 26 while at the same time the rod 34 is drawn back to the bobbin 32 by the magnetic force and the piston 11 is thus lowered. Since purified air supplied from the reservoir 30 is drawn into the cylinder 10 through the head chamber 26 as the piston 11 moves downward, external air will not be drawn into the cylinder 10 through the nozzle 27. The controller 40 will close the electromagnetic valve M for the next measurement when the piston 11 has reached its lowermost starting position.

The purified and compressed air flowing into the head chamber 26 while the electromagnetic valve M is opened can partially escape into the atmosphere through the nozzle 27. The compression ratio to be achieved by the compressor P should be adjusted not to allow the escaping air to deform the cornea of the subject eye The head chameber 26 is fed with air which has been drawn into the compressor P from outside and driven into the reservoir 30 by the compressor P. Alternatively, the head chamber may also be fed with air from any suitable container holding therein purified and compressed air. Further, the above described first and second embodiments are both constructed to use air as the gas for measurement by the tonometer. Any gas, for example, nitrogen or oxygen, however, may be used in place of air as long as it is harmless to the eye.

As described above, the device according to the invention is provided with means for feeding the tonometer head chamber with the gas for measurement through a passage which opens into said chamber and which does not include the nozzle through which the gas is to issue during measurement. Thus, according to the invention, the tonometer head chamber and the associated compression chamber are fed with the gas which is not from adjacent the subject eye. This means that airborn dust or tear drops scattered into air by the gas jet will not be drawn into the tonometer or the cylinder. The device of the invention is therefore advantageous from the point of view of hygiene.

THIRD EMBODIMENT

Figure 4:
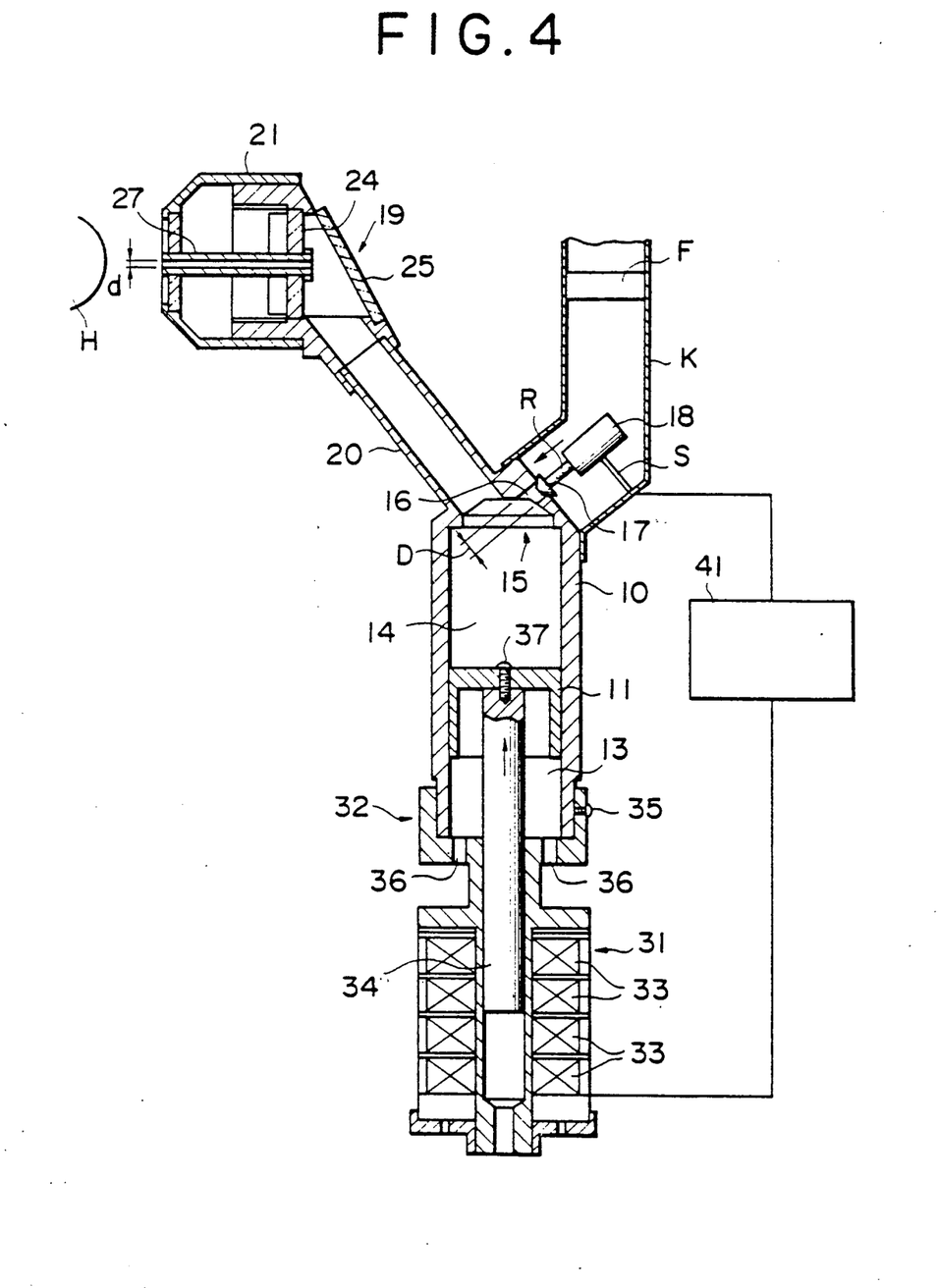
FIG. 4 is a cross sectional view of a third embodiment of the present invention.

FIG. 4 shows a third embodiment. Those elements which have equivalents in the first embodiment are designated by equivalent or identical reference characters and will not be described.

In FIG. 4, a suction port 16 is formed in the air outlet port 15 which in turn is formed in the end of the cylinder 10 in which the compression chamber 14 is defined. The suction port 16 forms part of the passage through which air is drawn into the cylinder from a region remote from the nozzle, and has a diameter D for which the following relationship holds:

$$D > 5d$$

where d is the diameter of the nozzle.

A suction tube K is secured to the outside of the cylinder, surrounding the suction port 16. The suction tube K has a support member S mounted therein, with a solenoid 18 secured to the support member S. A suction valve body 17 is formed on a rod R of the solenoid 18, which is arranged to open and close the suction port 16. The solenoid 18 is arranged to maintain the rod R in its projected position thus to close the suction port 16 when not energized, and maintain the rod in its retracted position when energized.

A controller 41 controls the linear d.c. motor 31 and the solenoid 18 in such a manner that the solenoid 18 is energized while a current is passed through the coils 33 such as to drive the piston downward. That is, when a negative pressure is established in the compression chamber 14, the solenoid 18 is energized to retract the rod R thereby to open the suction valve 17. Air is thus drawn through the filter F into the compression chamber 14 from a region remote from the nozzle which is located adjacent to the subject eye H. The suction port 16 and the suction valve 17 in combination constitute suction means.

The operation of the third embodiment will be described.

Figure 5:
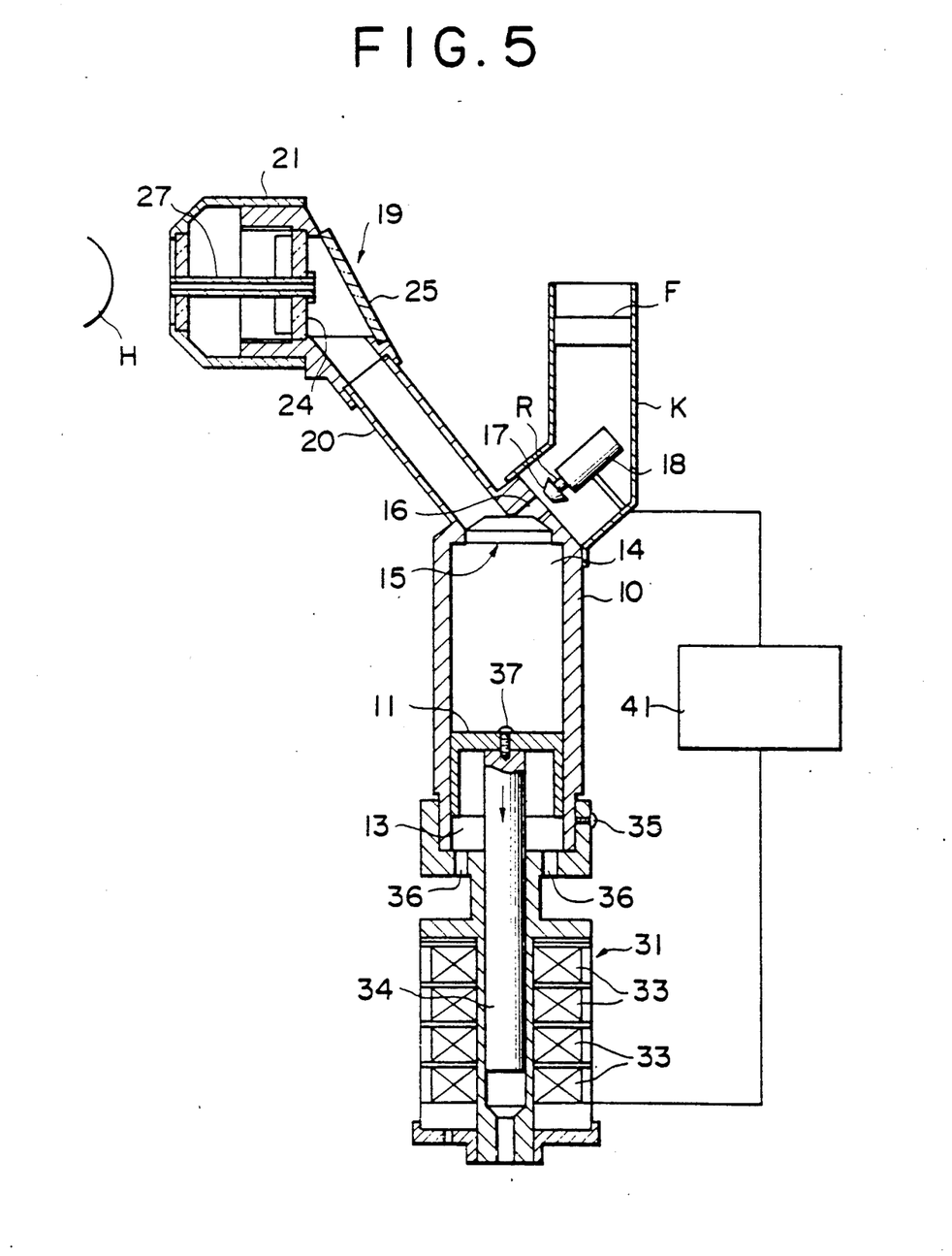
FIG. 5 is a cross sectional view of the third embodiment showing the piston at its lowered position.

A current is passed through the coils 33 of the linear d.c. motor 31 such as to polarize the bobbin 32 in the same direction as the permanent magnet rod 34. The rod 34 is driven toward the compression chamber by the magnetic interaction between the permanent magnet rod itself and the magnetic field established by the current through the coils 33; the piston 11 is moved upward with the rod 34 (FIG. 4). The piston 11 will compress the air within the compression chamber 14 while moving upward, and the thus compressed air will flow into the chamber 26 in the tonometer head 19 and will issue from the tonometer head 19 through the nozzle 27, forming an air jet. The air jet is directed toward the subject eye H for the measurement of the intraocular pressure. Upon completion of the issuance of the air jet, the solenoid 18 is energized to open the suction valve 17 as shown in FIG. 5, and at the same time the direction of the current through the coils 33 of the linear d.c. motor 32 is reversed to polarize the bobbin 31 in the opposite direction with respect to the permanent magnet rod 34. The rod 34 is then driven downward together with the piston 11 by the magnetic force (FIG. 5). The downward movement will reduce the pressure in the compression chamber 14 to a negative pressure. Since at that time the suction port 17 is opened by the energized solenoid 18, air from a region remote from the nozzle (i.e. air remote from the subject eye H) will flow into the compression chamber 14 through the filter F and through the suction port 16. Little amount of air will then be drawn into the cylinder through the nozzle 27, since the suction port 16 and the nozzle 27 are formed to have diameters D and d, respectively, which satisfy the relationship: D>5d. Therefore, the air around the subject eye, which may carry dust or scattered tear drops, will not be drawn into the tonometer, and thus the device can be kept hygienic.

FOURTH EMBODIMENT

Figure 6:
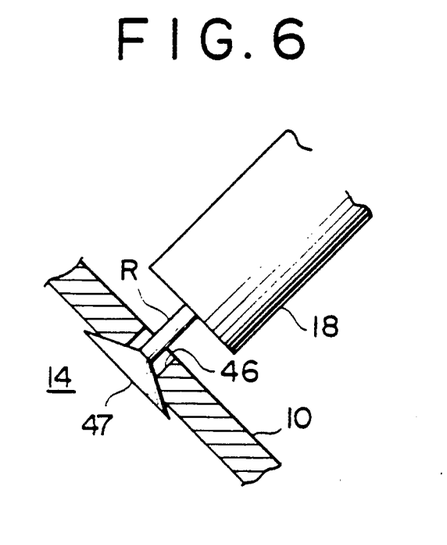
FIG. 6 is a view showing part of a fourth embodiment of the present invention.

FIG. 6 shows a fourth embodiment which differs from the embodiment shown in FIG. 4 and 5 only in that the valve body 47 to be operated by the solenoid 18' is located in the compresion chamber 14 so that the suction port 46 can easily be closed. The solenoid 18' used in this embodiment is arranged such that it will maintain the rod R in its projected position when energized and will retract the rod when deenergized.

What is claimed is:

1. A gas jet shooting device for use with a non-contact tonometer, of the type having a cylinder in which air is compressed by a piston arrangement, and a nozzle communicating with said cylinder to allow said compressed air to issue toward an eye examining position when said piston arrangement is in a first position, characterized by:
    means for reciprocating the piston arrangement in said cylinder body between the first position and a second position,
    suction means for allowing air to flow into said cylinder from a region from said nozzle when said piston arrangement is in the second position,
    a solenoid for actuating said suction means, and
    means for controlling said means for reciprocating the piston arrangement and said solenoid at predetermined intervals.

2. The gas jet shooting device for use with a non-contact tonometer as claimed in claim 1, in which said suction means comprises:
    a suction port provided in said portion of said cylinder in which air can be compressed, and
    a suction valve body for closing said suction port when the piston arrangement in said cylinder is approaching or in the first position and for opening said suction port when said piston arrangement in said cylinder is approaching or in the second position.

3. The air jet shooting device for use with a non-contact tonometer as claimed in claim 2, wherein said region remote from said nozzle for allowing air to flow into said cylinder comprises a suction tube.

4. The air jet shooting device for use with a non-contact tonometer as claimed in claim 3, wherein
   said suction tube includes a support member, mounted on the interior wall of said suction tube, and
   said solenoid for actuating the suction means is mounted on said support member within said suction tube.

5. The air jet shooting device for use with a non-contact tonometer as claimed in claim 4, wherein
   a rod extends from said solenoid toward said suction port, and
   said suction valve body, arranged to open and close said suction port, is attached to said rod extending from said solenoid.

6. An air jet shooting device for use with a non-contact tonometer comprising:
   a compression chamber supporting an upper compression condition and a lower compression condition,
   a nozzle attached to said compression chamber for ejecting compressed air from said compression chamber when in the higher compression condition,
   said nozzle having a diameter of d,
   a first path for communicating flow between said compression chamber and said nozzle,
   a second path remote from said nozzle for communicating flow between said compression chamber and ambient air,
   a suction port, communicating between said second path and said compression chamber, having a diameter D such that the relationship between the diameter of said suction port and the diameter of said nozzle is at least $D > 5d$, and
   a valve for said suction port which is open when said compression chamber is in the lower compression condition and closed when said compression chamber is in the higher compression condition.

7. The air jet shooting device for use with a non-contact tonometer as claimed in claim 6 wherein said compression chamber is operated by means for alternating said compression chamber between the upper compression condition and the lower compression condition.

8. An air jet shooting device for use with a non-contact tonometer, of the type having a cylinder in which air is compressed by a piston arrangement, characterized by:
   means for reciprocating the piston arrangement in said cylinder between a first position in which air is compressed and a second position,
   a nozzle communicating with said cylinder to allow said compressed air to issue toward an eye examining position when said piston arrangement is in the first position,
   suction means positioned for allowing air to flow into said cylinder from a region remote from said nozzle when said piston arrangement is in the second position,
   a motor for actuating said suction means, and
   means for controlling said means for reciprocating said piston arrangement and said motor at predetermined intervals.

9. The air jet shooting device for use with a non-contact tonometer as claimed in claim 8, in which said suction means comprises:
   a suction port provided in said portion of said cylinder in which air can be compressed, and
   a suction valve for closing said suction port when the piston arrangement in said cylinder is approaching or in the first position and for opening said suction port when said piston arrangement in said cylinder is approaching or in the second position.

10. The air jet shooting device for use with a non-contact tonometer as claimed in claim 9 wherein said region remote from said cylinder for allowing air to flow into said cylinder comprises a suction tube.

11. The air jet shooting device for use with a non-contact tonometer as claimed in claim 10 wherein said suction tube includes
    a support member, mounted on the interior wall of said suction tube, and
    said motor for actuating the suction means is mounted on said support member.

12. The air jet shooting device for use with a non-contact tonometer as claimed in claim 11 wherein
    said motor includes a rod extension, and
    said suction valve is attached to said rod extension.

13. The air jet shooting device for use with a non-contact tonometer as claimed in claim 12 wherein said nozzle has a diameter d and wherein said suction port has a diameter D such that the relationship between the diameter of said suction port and the diameter of said nozzle is at least $D > 5d$.

* * * * *